(12) United States Patent
Matsumoto et al.

(10) Patent No.: US 7,078,576 B2
(45) Date of Patent: Jul. 18, 2006

(54) PROCESS FOR PRODUCING ISOPROPYL CHLORIDE

(75) Inventors: Tomoko Matsumoto, Tokyo (JP); Tateo Nakano, Chiba (JP); Yutaka Yokoyama, Ibaraki (JP); Tomoji Makiguchi, Ibaraki (JP)

(73) Assignees: Kashima Chemical Company, Limited, Kashima-gun (JP); Asahi Glass Company, Limited, Tokyo (JP)

( * ) Notice: Subject to any disclaimer, the term of this patent is extended or adjusted under 35 U.S.C. 154(b) by 8 days.

(21) Appl. No.: 10/851,154

(22) Filed: May 24, 2004

(65) Prior Publication Data
US 2004/0215041 A1    Oct. 28, 2004

Related U.S. Application Data

(63) Continuation of application No. PCT/JP02/12515, filed on Nov. 29, 2002.

(30) Foreign Application Priority Data
Nov. 30, 2001   (JP) .............................. 2001-365647

(51) Int. Cl.
*C07C 17/00*   (2006.01)

(52) U.S. Cl. ...................................... 570/198; 570/197

(58) Field of Classification Search ................ 570/248, 570/250
See application file for complete search history.

(56) References Cited

U.S. PATENT DOCUMENTS

| | | | | |
|---|---|---|---|---|
| 2,033,374 A | * | 3/1936 | Gayer | ......................... 570/248 |
| 4,009,216 A |   | 2/1977 | Grolilg et al. | |
| 4,168,210 A | * | 9/1979 | Boozalis et al. | ................ 203/6 |
| 4,661,341 A |   | 4/1987 | Benedict et al. | |

FOREIGN PATENT DOCUMENTS

| | | |
|---|---|---|
| DE | 509265 | 9/1930 |
| DE | 1 805 805 | 6/1970 |
| DE | 1 801 716 | 11/1970 |
| FR | 1526687 | 4/1968 |
| GB | 1042705 | 9/1966 |
| JP | 50-130702 | 10/1975 |
| JP | 60-178831 | 9/1985 |

\* cited by examiner

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

The present invention is an industrially advantageous process for isopropyl chloride production in which the catalytic activity can be maintained under the milder reaction conditions than in the conventional processes, and which requires no special reactor.

Propylene and hydrogen chloride is reacted in a gas phase, in the presence of iron or a halogenated aluminum oxide (preferably, aluminum oxide reacted with hydrogen chloride). Preferably, a temperature during the reaction is 20 to 100° C., and a pressure of the reaction is 1013 to 3039 hPa (absolute pressure).

17 Claims, No Drawings

PROCESS FOR PRODUCING ISOPROPYL CHLORIDE

TECHNICAL FIELD

The present invention relates to a process for producing isopropyl chloride.

BACKGROUND ART

As conventional processes for producing isopropyl chloride, the following processes are known.

(1) A method of reacting isopropyl alcohol with hydrochloric acid (DE509265, BP1042705).

(2) A method of reacting propylene with hydrochloric acid or hydrogen chloride in a solvent (FR1526687, DE1805805, DE1801716, USP4661341, JP-A-60-178831).

(3) A method of reacting propylene with hydrogen chloride in a gas phase, in the presence of aluminum oxide which is not reacted with a hydrogen halide (JP-A-50-130702).

However, the conventional processes have following problems.

In the process (1), the conversion is low. In the process (2), when the reaction temperature is high, polymerization of propylene occurs, and the catalytic activity remarkably decreases. When the reaction temperature is low, the conversion decreases. Further, in the liquid containing the reaction product, the corrosive catalyst is accompanied, whereby there is a problem that the purification process may be complicated, or the purification apparatus is required to be made of an expensive corrosion-resistant material. Further, in the process (3), from a practical standpoint, it was necessary to maintain the temperature at the time of the reaction at a high temperature of about 100° C. or higher, and the pressure at a high pressure of about 5 atm, namely about 5065 hPa, respectively. Further, hydrogen chloride had to be supplied also at a high pressure. In order to maintain the pressure of the hydrogen chloride to be high, it is required to employ an expensive apparatus made of a corrosion-resistant material. Thus, the conventional processes have been disadvantageous as industrial processes.

DISCLOSURE OF THE INVENTION

It is an object of the present invention to solve the above problems. The present invention provides a process for producing isopropyl chloride, which comprises reacting propylene and hydrogen chloride in a gas phase, in the presence of iron or a halogenated aluminum oxide.

BEST MODE FOR CARRYING OUT THE INVENTION

In the present invention, the reaction of propylene and hydrogen chloride is carried out in the presence of iron or a halogenated aluminum oxide.

The iron is preferably iron having impurities reduced as little as possible, i.e. the iron is preferably one having a purity of 90% to 100% (mass basis, the same applies hereinafter), and more preferably one having a purity of 95% to 100%, and further more preferably one having a purity of 98% to 100%. The iron in the present invention, may or may not be subjected to pre-treatment such as activation treatment by contacting it with e.g. hydrogen chloride. When the pre-treatment is to be carried out, a usual pre-treatment method can be suitably applied. Further, the form of the iron is not particularly limited, but it is preferably be iron of linear, net, or spherical form, having a large surface area, whereby the effect as a catalyst increases.

Iron is generally considered to have a low catalytic activity. However, the iron present in the reaction system in this invention, is considered to have the same effect as that of ferric chloride which is one of the Friedel-Crafts catalysts, as the surface is activated by the reaction with hydrogen chloride. The surface area of the iron is preferably at least 150 mm$^2$/g, more preferably at least 1500 mm$^2$/g, further more preferably at least 3000 mm$^2$/g.

Further, the halogenated aluminum oxide in the present invention, is preferably aluminum oxide reacted with a hydrogen halide. As the hydrogen halide, hydrogen fluoride, hydrogen chloride, hydrogen bromide and hydrogen iodide may, for example, be mentioned. Among these hydrogen halides, hydrogen chloride is most preferred, since it is available at a low price, it is used in the reaction of propylene and hydrogen chloride in the present invention, and further, it can be easily handled.

The form of the aluminum oxide is preferably a spherical or block form. In the case of a spherical form, the average particle size is preferably from 0.5 to 5 mm. In the case of a block form, it is preferably one having such a size that it can be sieved by a sieve of 0.5 to 5 mm. Further, the aluminum oxide in the present invention is preferably one having a pore volume of from 0.05 to 2 ml/g, more preferably from 0.1 to 1 ml/g.

As a method of reacting the aluminum oxide and a hydrogen halide, a method of packing the aluminum oxide in a reactor, and then supplying the hydrogen halide to the reactor, may, for example, be mentioned. This hydrogen halide may be in a liquid form or in a gas form. From the point that it is possible to treat a large amount effectively, the hydrogen halide in a gas form is preferred. At the time of treatment, the aluminum oxide and the hydrogen halide may sometimes vigorously be reacted, whereby heat generation or a formation of water may take place. Therefore, it is preferred to dilute the hydrogen halide by using an inert gas to the aluminum oxide. The inert gas can be a medium which removes the heat of the reaction of the aluminum oxide and the hydrogen halide from the reactor. Further, in a case where water is formed, it is preferred to remove it out of the reactor together with the inert gas. As the inert gas, nitrogen gas, helium gas, and argon gas may, for example, be mentioned.

When the aluminum oxide packed in the reactor is reacted with the hydrogen halide in a gas form, it is preferred to dilute it so that the amount of the hydrogen halide would be from 0.1 to 10 vol %, particularly preferably from 2 to 7 vol %, to the total amount of the hydrogen halide and the inert gas, in the initial stage of the reaction. Then, it is preferred to continue to supply the diluted hydrogen halide till the heat of the reaction is no longer generated in the reactor. Further, after completion of generation of the heat of the reaction, it is preferred to raise the concentration of the hydrogen halide so that the concentration of the hydrogen halide will finally be 100 vol % (namely, the hydrogen halide which is not diluted with the inert gas). If the concentration of the hydrogen halide is raised, the heat of the reaction will usually be generated again. It is preferred to raise the concentration of the hydrogen halide gradually in order to avoid abrupt generation of such heat of the reaction. Further, it is preferred to continue to supply 100 vol % of the hydrogen halide till the heat of the reaction is no longer generated. Further, when the aluminum oxide is reacted with the hydrogen halide, it is preferred to carry out the reaction so that the temperature in the reactor will not exceed 200° C.

due to the heat of the reaction. The amount of the aluminum oxide to be reacted with the hydrogen halide, is preferably such an amount that the temperature of the aluminum oxide will not exceed 200° C. at the time of reaction.

The reactor to be packed with the aluminum oxide is preferably one having a structure which can be cooled. When the reactor having such a structure is used, the aluminum oxide reacted with the hydrogen halide can be used to the reaction of propylene and hydrogen chloride, as it is packed in the reactor. Particularly, it is preferred to use a reactor having a structure provided with e.g. a jacket cooler, as the reactor to carry out the reaction of the aluminum oxide and the hydrogen halide, since it is thereby easy to control the reaction when the following reaction of the propylene and the hydrogen chloride is carried out. Further, the aluminum oxide reacted with the hydrogen halide may be transferred to another reactor to carry out the reaction of propylene and hydrogen chloride of the present invention.

The reaction of propylene and hydrogen chloride in the present invention is preferably carried out by supplying propylene in a gas form and hydrogen chloride in a gas form to the reactor or the like packed with the iron or the halogenated aluminum oxide, followed by gas phase reaction. It is preferred that propylene and hydrogen chloride are preliminarily mixed and then supplied to the reactor, whereby the efficiency of the reaction will be good. As the material for the reactor, a common material such as iron, stainless steel or glass may be preferably used.

The temperature for reacting propylene and hydrogen chloride is preferably from 20° C. to 100° C., more preferably from 40° C. to 60° C. Here, it is preferred to control the supply amount and the supply temperature of propylene and hydrogen chloride, so that the reaction temperature will be within the above temperature range, and further, the cooling of the reactor is carried out as the case requires. When the temperature during the reaction is at least 20° C., condensation of formed isopropyl chloride will be little, and the surface of the iron or the aluminum oxide will not be wetted with the isopropyl chloride, whereby the catalytic effect will be maintained for a long term, such being desirable. Further, in a case where the temperature during the reaction is at most 100° C., polymerization of propylene is reduced, such being desirable. The reduction of the polymerization can avoid the problem that the produced oligomer covers the surface of the catalyst whereby the catalytic effect is decreased.

Further, the pressure at the time of reacting propylene and hydrogen chloride in the present invention, is preferably from 900 to 3039 hPa (mass basis, hereinafter the same applies), more preferably from 1013 to 3039 hPa, further more preferably from 2026 to 3039 hPa. It is preferred that the pressure of the reaction is at least 900 hPa, since the boiling point of isopropyl chloride will be high, and the produced isopropyl chloride can be easily recovered. Further, it is preferred that the pressure of the reaction is at most 3039 hPa, since it is thereby not required to employ an expensive apparatus having acid resistance and capable of raising the pressure of hydrogen chloride to a high level.

The molar ratio of propylene and hydrogen chloride is not particularly limited. For the purpose of increasing the efficiency for recovering isopropyl chloride, maintaining the reaction pressure, reducing corrosion of the apparatus due to remaining unreacted hydrogen chloride, or the like, it is preferred to use propylene in an amount of from equivalent to excess, the amount of propylene to hydrogen chloride is preferably from 1 to 1.5 times by mol, more preferably from 1 to 1.1 times by mol.

The space velocity (SV) [unit: /hr] for supplying propylene and hydrogen chloride to the reactor, is not particularly limited so long as it is a level within such a range that the above temperature and pressure condition can be maintained, usually it is preferred that SV=100 to 1000/hr. Here, the space velocity is the ratio of the volume velocity for supplying the material (F) [unit: $m^3$/hr] to the volume of the reactor (V) [unit: $m^3$]. Namely, SV=F/V [unit: /hr].

Isopropyl chloride formed in the process of the present invention, can be obtained usually as a gaseous product. The gaseous isopropyl chloride is preferably cooled and collected as a liquid product. Further, the isopropyl chloride is preferably purified, as the case requires, as it is in a gaseous form, or after liquefied. The purification method is not particularly limited, and usual deacidification treatment, column chromatography, distillation or the like, may be mentioned. Isopropyl chloride formed by the process of the present invention is a known compound, and it may be used, as it is, or after converting it to another product.

In the process of the present invention, the reason why the catalytic activity can be maintained for a long term and the reaction can be carried out in the milder reaction conditions, is not surely obvious, but it is considered as follows. Namely, with the catalyst reacted with a hydrogen halide, the catalyst is usually too activated, whereby polymerization reaction of propylene itself is accelerated in the reaction of propylene and hydrogen chloride. And, an oligomer of propylene formed by the polymerization covers the surface of the catalyst and rapidly reduces the catalytic activity. However, the catalyst in the present invention, especially the halogenated aluminum oxide, has a suitable activity, whereby it is considered that the reaction of hydrogen chloride and propylene is more accelerated than the polymerization of propylene, and further, the catalytic activity can be maintained by avoiding the inconvenience caused by the polymerization of propylene.

Isopropyl chloride obtained by the process of the present invention, is useful as a starting material for an antifouling paint to be used as a paint for ship's bottom, an intermediate for a medicine or an agricultural chemical, or the like.

EXAMPLES

Now, the present invention will be described in detail with reference to Examples (Examples 1 to 8) and Comparative Example (Example 9). However, it should be understood that the present invention is by no means restricted by such specific Examples.

Example 1

6 g of spherical aluminum oxide (average particle size: 3 mm, pore volume: 0.5 ml/g) was packed in a pipe type reaction tube made of stainless steel having an internal diameter of 20 mm and a length of 300 mm and provided with a jacket. While the reaction tube was cooled by water at a temperature of 25° C., hydrogen chloride gas diluted with nitrogen gas to 3 vol % (temperature: 60° C., pressure: 1013 hPa, velocity: 1 L/hr), was supplied thereto for 2 hours. Then, while the concentration of hydrogen chloride was gradually raised, the diluted hydrogen chloride gas was supplied to the reaction tube, so that the concentration of hydrogen chloride was 100 vol % after two hours. Further, the supply of the hydrogen chloride gas was continued till the heat generation in the reaction tube was no longer observed to carry out the halogenation treatment of the aluminum oxide.

The mixed gas of propylene and hydrogen chloride (propylene:hydrogen chloride=1.05:1 (molar ratio)) was introduced at SV=200/hr into the reaction tube packed with the aluminum oxide treated by halogenation, to adjust the pressure in the reaction tube to 2026 hPa and the outlet temperature of the reaction tube to 50±10° C. After the space velocity of the mixed gas, the pressure in the reaction tube and the outlet temperature of the reaction tube were adjusted to the above values (this may be referred to also as after the stabilization, the same applies hereinafter), the gas at the outlet of the reaction tube was analyzed by gas chromatography. The conversion of hydrogen chloride was 99%, the conversion of propylene was 94%, and the selectivity for isopropyl chloride was 98%. Furthermore, the results after 100 hours and 200 hours, when the mixed gas of propylene and hydrogen chloride was continuously supplied for 200 hours, are shown in Table 1. No decrease was observed in any of the conversion and the selectivity.

Example 2

The operation was carried out in the same manner as in Example 1 except that the spherical aluminum oxide was changed to block-form aluminum oxide (sieved by a sieve of 3 mm, pore volume: 0.5 ml/g). The results are shown in Table 1.

Example 3

The operation was carried out in the same manner as in Example 1 except that the pressure in the reaction tube was changed from 2026 hPa to 1013 hPa. The results are shown in Table 1.

Example 4

The operation was carried out in the same manner as in Example 1 except that the hydrogen chloride gas reacted with aluminum oxide was changed to hydrogen fluoride gas. The results are shown in Table 1.

Example 5 to 7

The operation was carried out in the same manner as in Example 1 except that the space velocity was changed as shown in table 2.

Example 8

About 5 g of an iron wire (purity: 99.9%) having a radius of 0.05 mm (surface areas: about 5000 mm$^2$/g), was packed in the same reaction tube as in Example 1, and a mixed gas of propylene and hydrogen chloride (propylene:hydrogen chloride=1.05:1 (molar ratio)) was introduced at SV=100/hr, to adjust the pressure in the reaction tube to 2026 hPa, and the outlet temperature of the reaction tube to 60±10° C. After the stabilization, the gas at the outlet of the reaction tube was analyzed by gas chromatography, and the conversion of hydrogen chloride was 90%, the conversion of propylene was 86%, and the selectivity for isopropyl chloride was 98%. Further, the results after 100 hours and 200 hours, when the mixed gas of propylene and hydrogen chloride was continuously supplied for 200 hours, are shown in Table 1. The catalytic activity was maintained, and neither the conversion nor the selectivity was changed.

Example 9 (Comparative Example)

The operation was carried out in the same manner as in Example 1 except that aluminum oxide was used as it is, without subjecting it to halogenation treatment. The results are shown in Table 1. After the stabilization, the gas at the outlet of the reaction tube was analyzed by gas chromatography, and the conversion of hydrogen chloride was 99%, the conversion of propylene was 93%, and the selectivity for isopropylene chloride was 98%. Further, the reaction was continued for 100 hours, and as a result, the conversion decreased to 10% due to a decrease of the catalytic activity.

In Tables, the conversion represents the conversion of propylene, and the selectivity represents the selectivity for isopropyl chloride.

TABLE 1

|  | Immediately after stabilization | | 100 hours after stabilization | | 200 hours after stabilization | |
|---|---|---|---|---|---|---|
|  | Conversion | Selectivity | Conversion | Selectivity | Conversion | Selectivity |
| Ex. 1 | 94% | 98% | 94% | 98% | 94% | 98% |
| Ex. 2 | 94% | 98% | 94% | 98% | 94% | 98% |
| Ex. 3 | 94% | 98% | 94% | 98% | 94% | 98% |
| Ex. 4 | 94% | 98% | 94% | 98% | 94% | 98% |
| Ex. 8 | 86% | 98% | 86% | 98% | 86% | 98% |
| Ex. 9 | 94% | 98% | 10% | 98% | — | — |

TABLE 2

|  | Space velocity SV (/hr) | Immediately after stabilization | | 100 hours after stabilization | | 200 hours after stabilization | |
|---|---|---|---|---|---|---|---|
|  |  | Conversion | Selectivity | Conversion | Selectivity | Conversion | Selectivity |
| Ex. 5 | 100 | 94% | 98% | 94% | 98% | 94% | 98% |
| Ex. 6 | 500 | 91% | 96% | 91% | 98% | 91% | 98% |
| Ex. 7 | 1000 | 86% | 90% | 86% | 98% | 86% | 98% |

INDUSTRIAL APPLICABILITY

According to the process of the present invention, isopropyl chloride can be produced in advantageous conditions as compared with conventional processes. Namely, the process of the present invention can be carried out at a low temperature and at a low pressure, as compared with the conventional processes. Further, in the process of the present invention, the conversion of propylene and hydrogen chloride is high, whereby the remaining hydrogen chloride can be reduced, and post-treatment will be easy, and corrosion of the reaction apparatus can be suppressed. Further, it is not required to employ an expensive apparatus made of a corrosion-resistant material. Further, the catalytic activity can be maintained for a long term, and a continuous production process for a long term is possible. And further, isopropyl chloride can be produced by using propylene which is cheaper than isopropyl alcohol. From the foregoing, the process of the present invention is an excellent process, which is useful for an industrial operation.

The entire disclosure of Japanese Patent Application No. 2001-365647 filed on Nov. 30, 2001 including specification, claims and summary is incorporated herein by reference in its entirety.

What is claimed is:

1. A process for producing isopropyl chloride, which comprises reacting propylene and hydrogen chloride in a gas phase, in the presence of a halogenated aluminum oxide.

2. The process according to claim 1, wherein the halogenated aluminum oxide is aluminum oxide reacted with a hydrogen halide.

3. The process according to claim 1, wherein temperature at the time of reacting propylene and hydrogen chloride is from 20 to 100° C.

4. The process according to claim 1, wherein the pressure at the time of reacting propylene and hydrogen chloride is from 900 to 3039 hPa (absolute pressure).

5. A process for producing isopropyl chloride, which comprises reacting propylene and hydrogen chloride in a gas phase, in the presence of aluminum oxide obtained by preliminarily reacting a hydrogen halide and aluminum oxide.

6. A process for producing isopropyl chloride, which comprises packing aluminum oxide in a reactor, preliminarily reacting it with a hydrogen halide, and then introducing a mixed gas of propylene and hydrogen chloride to the reactor to react propylene and hydrogen chloride in a gas phase.

7. The process according to claim 6, wherein the outlet temperature of the reactor is from 40 to 70° C.

8. The process according to claim 6, wherein the pressure in the reactor is from 900 to 3039 hPa.

9. The process according to claim 6, wherein the space velocity of the mixed gas is from 100 to 1000/hr.

10. The process according to claim 6, wherein the average particle size of the aluminum oxide is from 0.5 to 5 mm.

11. The process according to claim 6, wherein temperature at the time of reacting propylene and hydrogen chloride is from 20 to 100° C.

12. The process according to claim 11, wherein temperature at the time of reacting propylene and hydrogen chloride is from 40 to 60° C.

13. The process according to claim 8, wherein the pressure in the reactor is from 1013 to 3039 hPa.

14. The process according to claim 13, wherein the pressure in the reactor is from 2026 to 3039 hPa.

15. The process according to claim 2, wherein the hydrogen halide is hydrogen chloride.

16. The process according to claim 5, wherein the hydrogen halide is hydrogen chloride.

17. The process according to claim 6, wherein the hydrogen halide is hydrogen chloride.

* * * * *